(12) United States Patent
Pather et al.

(10) Patent No.: US 6,576,250 B1
(45) Date of Patent: Jun. 10, 2003

(54) PHARMACEUTICAL COMPOSITIONS FOR RECTAL AND VAGINAL ADMINISTRATION

(75) Inventors: S. Indiran Pather, Plymouth, MN (US); Joseph R. Robinson, Madison, WI (US); Jonathan D. Eichman, Ann Arbor, MI (US); Rajendra K. Khankari, Maple Grove, MN (US); John Hontz, Plymouth, MN (US)

(73) Assignee: Cima Labs Inc., Eden Prairie, MN (US)

( * ) Notice: Subject to any disclaimer, the term of this patent is extended or adjusted under 35 U.S.C. 154(b) by 0 days.

(21) Appl. No.: 09/664,870

(22) Filed: Sep. 19, 2000

Related U.S. Application Data

(63) Continuation-in-part of application No. 09/327,814, filed on Jun. 8, 1999, now Pat. No. 6,200,604, which is a continuation of application No. 09/277,424, filed on Mar. 26, 1999, now abandoned, application No. 09/664,870, which is a continuation-in-part of application No. 09/302,105, filed on Apr. 29, 1999, now Pat. No. 6,350,470.
(60) Provisional application No. 60/083,391, filed on Apr. 29, 1998, and provisional application No. 60/079,652, filed on Mar. 27, 1998.

(51) Int. Cl.$^7$ .............................................. A61K 9/02
(52) U.S. Cl. ..................................................... 424/436
(58) Field of Search ................................ 424/430, 433, 424/436, 464, 451, 466

(56) References Cited

U.S. PATENT DOCUMENTS

| | | | |
|---|---|---|---|
| 3,888,976 A | 6/1975 | Mlkvy et al. .................. 424/44 |
| 3,961,041 A | 6/1976 | Nishimura et al. ............ 424/35 |
| 3,972,995 A | 8/1976 | Tsuk et al. ..................... 424/28 |
| 4,289,751 A | 9/1981 | Windheuser ................... 424/35 |
| 4,493,848 A | 1/1985 | LaHann et al. .............. 424/324 |
| 4,503,031 A | 3/1985 | Glassman ...................... 424/15 |
| 4,639,368 A | 1/1987 | Niazi et al. .................... 424/48 |
| 4,853,211 A | * 8/1989 | Kurobe et al. ................. 424/44 |
| 5,002,771 A | * 3/1991 | Purkaystha et al. ......... 424/433 |
| 5,135,752 A | 8/1992 | Snipes ......................... 424/486 |
| 5,178,878 A | 1/1993 | Wehling et al. ............. 424/466 |
| 5,223,264 A | 6/1993 | Wehling et al. ............. 424/466 |
| 5,458,879 A | 10/1995 | Singh et al. ................. 424/400 |
| 5,607,697 A | 3/1997 | Alkire et al. ................ 424/495 |
| 5,646,151 A | 7/1997 | Kruse et al. |
| 5,656,284 A | 8/1997 | Balkin ......................... 424/435 |
| 5,958,455 A | 9/1999 | Roser et al. ................. 424/489 |
| 5,958,458 A | 9/1999 | Norling et al. .............. 424/490 |
| 6,117,912 A | 9/2000 | DiSanto |
| 6,129,906 A | 10/2000 | Steventon .................... 424/49 |
| 6,264,981 B1 | 7/2001 | Zhang et al. |

FOREIGN PATENT DOCUMENTS

WO  WO 91/04757  4/1991

OTHER PUBLICATIONS

Eichman, J. D., and Robinson, J.R., "Mechnanistic Studies on Effervescent–Induced Permeability Enhancement" Pharm. Res. 15(6):925–30 (1998).

Eichman, J.D., Thesis "Mechanistic Studies on Effervescent–Induced Permeability Enhancement" (catalogued at the University of Wisconsin–Madison on Sep. 18, 1998) (on file with the University of Wisconsin–Madison).

Squier, C.A., and Wertz, P.W., "Structure and Function of the Oral Mucosa and Implications for Drug Delivery" *Oral Mucosal Drug Delivery*, Ch. 1, pp. 1–19 (1996).

Wertz et al., "Biochemical Basis of the Permeability Barrier in Skin and Oral Mucosa" *Oral Mucosal Drug Delivery*, Ch. 2, pp. 27–41 (1996).

Zhang, H., and Robinson, J.R., "Routes of Drug Transport Across Oral Mucosa" *Oral Mucosal Drug Delivery*, Ch. 3, pp. 51–61 (1996).

Aungst, B.J., "Oral Mucosal Permeation Enhancement: Possibilities and Limitations" *Oral Mucosal Drug Delivery*, Ch. 4, pp. 65–81 (1996).

Zhang, H., and Robinson, J.R., "In Vitro Methods for Measuring Permeability of the Oral Mucosal" *Oral Mucosal Drug Delivery*, Ch. 5, pp. 85–97 (1996).

Audus, K.L., "Buccal Epithelial Cell Cultures as a Model to Study Oral Mucosal Drug Transport and Metabolism" *Oral Mucosal Drug Delivery*, Ch. 6, pp. 101–15 (1996).

Rathbone et al., "In Vivo Techniques for Studying the Oral Mucosal Absorption Characteristics of Drugs in Animals and Humans" *Oral Mucosal Drug Delivery*, Ch. 7, pp. 121–51 (1996).

Weatherell et al., "The Flow of Saliva and Its Influence on the Movement, Deposition and Removal of Drugs Administered to the Oral Cavity" *Oral Mucosal Drug Delivery*, Ch. 8, pp. 157–87 (1996).

Schenkels et al., "Salivary Mucins: Their Role in Oral Mucosal Barrier Function and Drug Delivery" *Oral Mucosal Drug Delivery*, Ch. 9, pp. 191–211 (1996).

Kellaway, I.W., and Warren, S.J., "Mucoadhesive Hydrogels for Buccal Delivery" *Oral Mucosal Drug Delivery*, Ch. 10, pp. 221–237 (1996).

Rathbone et al., "Systemic Oral Mucosal Drug Delivery and Delivery Systems" *Oral Mucosal Drug Delivery*, Ch. 11, pp. 241–275 (1996).

(List continued on next page.)

Primary Examiner—James M. Spear
(74) Attorney, Agent, or Firm—Lerner, David, Littenberg, Krumholz & Mentlik, LLP

(57) ABSTRACT

The pharmaceutical compositions of the present invention comprise rectally and vaginally administerable dosage forms that contain effervescent agents as penetration enhancers for drugs. Effervescence occurs in the rectum or vagina, once the dosage form is administered or at a predetermined time following administration. The effervescent agents can be used alone or in combination with pH adjusting substance, which further promote dissolution and absorption of the active ingredient.

9 Claims, No Drawings

OTHER PUBLICATIONS

DeGrande et al., "Specialized Oral Mucosal Drug Delivery Systems: Patches" *Oral Mucosal Drug Delivery*, Ch. 12, pp. 285–313 (1996).

Rassing, M.R., "Specialized Oral Mucosal Drug Delivery Systems: Chewing Gum" *Oral Mucosal Drug Delivery*, Ch. 13, pp. 319–353 (1996).

Soskolone, W.A., and Friedman, M., "Intra–Periodontal Pocket Drug Delivery Systems" *Oral Mucosal Drug Delivery*, Ch. 14, pp. 359–373 (1996).

Sasahara et al., "Dosage Form Design for Improvement of Bioavailibility of Levodopa IV: Possible Causes of Low Bioavailability of Oral Levodopa in Dogs" J. Pharm. Sci. 70(7):730–33 (1981).

Sasahara et al., "Dosage Form Design for Improvement of Bioavailability of Levodopa III: Influence of Dose on Pharmacokinetic Behavior of Levodopa in Dogs and Parkinsonian Patients" J. Pharm. Sci. 69(12):1374–1378 (1980).

Sasahara et al., "Dosage Form Design for Improvement of Bioavailability of Levodopa II: Bioavailability of Marketed Levodopa Preparations in Dogs and Parkinsonian Patients" J. Pharm. Sci. 69(3):261–65 (1980).

Sasahara et al., "Dosage Form Design for Improvement of Bioavailability of Levodopa V: Absorption and Metabolism of Levodopa in Intestinal Segments of Dogs" J. Pharm. Sci. 70(10):1157–60 (1981).

Nishimura et al., "Dosage Form Design for Improvement of Bioavailability of Levodopa VI: Formulation of Effervescent Enteric–Coated Tablets" J. Pharm. Sci. 73(7):942–46 (1984).

\* cited by examiner

PHARMACEUTICAL COMPOSITIONS FOR RECTAL AND VAGINAL ADMINISTRATION

The present application is a continuation-in-part of application Ser. No. 09/302,105, filed Apr. 29, 1999, now U.S. Pat. No. 6,350,470 which in turn claims the benefit of U.S. Provisional Patent Application Ser. No. 60/083,391, filed Apr. 29, 1998, the disclosures of which are hereby incorporated by reference. The present application is also a continuation-in-part of application Ser. No. 09/327,814, filed Jun. 8, 1999, now U.S. Pat. No. 6,200,604 which in turn is a continuation of application Ser. No. 09/277,424, filed Mar. 26, 1999, now abandoned which in turn claims the benefit of U.S. Provisional Patent Application Ser. No. 60/079,652, filed Mar. 27,1998, the disclosures of which are hereby incorporated by reference.

FIELD OF THE INVENTION

The present application relates to pharmaceutical compositions and methods of delivering active ingredients through the rectum or vagina, and in particular to compositions and methods using effervescent agents as penetration enhancers to promote rectal or vaginal delivery of an active ingredient.

BACKGROUND OF THE INVENTION

Although generally not well accepted, various proposals have been advanced for rectal and vaginal administration of drugs. Because some veins in the rectum and vagina lead directly to the general circulation, when drugs are administered through the rectum or vagina, they have the advantage of bypassing the gastrointestinal and heptic metabolism process (i.e., reducing the first-pass effect). This can lead to faster onset of action and/or improved bioavailability of a drug. In addition, delivery of a drug through the rectum and vagina can be useful for patients unable or unwilling to take drugs orally or intravenously.

To improve the bioavailability of poorly absorbed drugs across the rectal and vaginal mucosa, penetration enhancers have been employed. Penetration enhancers are typically low molecular weight compounds, which enhance drug absorption across the mucosal membrane. There are generally five major classes of penetration enhancers: (1) bile salts and their derivatives (e.g., taurcholate, deoxcholate, and glycocholate); (2) chelators (e.g., citric acid, enamines, EDTA); (3) fatty acids and their derivatives (e.g., arachidonic acid, oleic acid, sodium caprylate, monoolein); (4) surfactants (e.g, SDS, polyoxyethylene-20-cetylether); and nonsurfactants (e.g., 1-alkylazacycloalkanone unsaturated ureas). Penetration enhancers are thought to increase drug permeability by affecting the membrane transport pathways and/or reducing the barrier effect of the mucosal lining.

Although generally effective, many of the penetration enhancers referred to in the current literature damage the absorbing tissues, often causing extensive tissue damage. Moreover, some penetration enhancers are also known to be toxic, such as bile salts, and therefore their use has been very limited. Accordingly, due to their side effects, penetration enhancers are often not a practical solution to the problem of poor bioavailability in the administration of active ingredients through rectum, vagina and elsewhere.

Therefore, there is a need for safe and effective penetration enhancers for the delivery of active ingredients across the rectal and vaginal mucosa.

SUMMARY OF THE INVENTION

The pharmaceutical compositions of the present invention comprise rectal or vaginal dosage forms containing an active ingredient in combination with an effervescent penetration enhancer for improving absorption of the active ingredient across the rectal and vaginal mucosa membranes, respectively. The effervescent agent can be used alone or in combination with a pH adjusting substance that alters the pH of the localized environment of the site of dissolution and absorption in the rectum or vagina to further improve dissolution and absorption.

DETAILED DESCRIPTION OF THE PREFERRED EMBODIMENTS

The pharmaceutical compositions of the present invention comprise rectally and vaginally administrable active ingredients in combination with an effervescent agent for influencing absorption of a drug in the rectum or vagina, respectively. Effervescence leads to an increase in the rate and/or the extent of absorption of the drugs, and in particular, drugs that are known or suspected of having poor bioavailability. It is believed that such increase can result from reducing the thickness and/or the viscosity of the mucus layer; alteration of the tight junctions between cells, thus promoting absorption through the paracellular route; inducing a change in the cell membrane structure, thus promoting transcellular absorption; and increasing the hydrophobic environment within the cellular membrane.

The pharmaceutical compositions include an active ingredient, which is administerable through the rectum or vagina, depending on the selected route of administration, and an amount of effervescent agent effective to aid in penetration of the drug in the rectum or vagina, respectively. The amount of effervescent employed must not merely permit rapid dispersion of the medicament, but must aid in penetration of the drug across the rectal or vaginal mucosa. In this regard, the pharmaceutical compositions of the present invention may be distinguished from other effervescent compositions on the basis of the amount of effervescent material that they contain.

The term "effervescent penetration enhancer" includes compounds which evolve gas. The preferred effervescent penetration enhancers evolve gas by means of a chemical reaction which takes place upon exposure of the effervescent penetration enhancer to small amounts of water and other fluids in the rectum or vagina, respectively. Such water-activated materials must be kept in a generally anhydrous state and with little or no absorbed moisture or in a stable hydrated form, since exposure to water will prematurely disintegrate the composition. The acid and base sources may be any which are safe for human or mammalian use. Suitable sources include acid and hydrite antacids such as, for example, citric, tartaric, amalic, fumeric, adipic, and succinics. Suitable base sources include carbonate sources, such as dry solid carbonate and bicarbonate salt, such as, preferably, sodium bicarbonate, sodium carbonate, potassium bicarbonate and potassium carbonate, magnesium carbonate and the like. The effervescent penetration enhancers of the present invention are not, however, limited to those that are based upon a reaction that forms carbon dioxide. Reactants which evolve oxygen or other gases and which are safe for human or mammalian use are also considered within the scope of the present invention.

The pharmaceutical compositions of the present invention should preferably contain at least about twice as much base as active ingredient (on a weight basis) together with the proportionate amount of an appropriate acid for generating the effervescent reaction. More preferably, the pharmaceutical compositions should contain at least about three times as much base as active ingredient (on a weight basis) together with the proportionate amount of an appropriate acid. It is particularly preferred that sufficient effervescent material be provided such that the evolved gas is more than 5 $cm^3$, upon exposure of the composition to an aqueous environment in the rectum or vagina, respectively. These high concentrations of effervescent agents are needed to generate effervescence in sufficient amounts to promote permeability and absorption of the active ingredient across the rectal and vaginal mucosa. However, the amount of effervescent agent must be optimized for each specific active ingredient and for delivery in the rectum or vagina, respectively.

The pharmaceutical compositions may also include one or more pH adjusting substances. For active ingredients that are weakly acidic or weakly basic, the pH of the aqueous environment can influence the relative concentrations of the ionized and the unionized forms of the active ingredient present in solution, according to the Henderson-Hasselbach equation. The pH of solutions in which an effervescent couple with equimolar amounts of base and acid has dissolved is slightly acidic due to the evolution of $CO_2$. Thus, the pH of the localized environment of the rectum or vagina (i.e., the contents of the rectum or vagina in immediate contact with the composition, including any active ingredient dissolved from the composition) may be altered to achieve desired relative proportions of ionized and unionized active ingredients by incorporating in the compositions certain pH adjusting substances.

Suitable pH adjusting substances include any pH adjusting substance that is safe for mammalian use. More preferably, the pH adjusting substances include any weak acid or weak base. These include, but are not limited to, any of the acids or bases previously mentioned as the effervescent components, including, sodium carbonate, potassium carbonate, disodium hydrogen phosphate, sodium dihydrogen phosphate, and the equivalent potassium salts.

The compositions may be administered in any dosage form suitable for delivery of an active ingredient to the rectum or vagina, respectively. For rectal administration, these compositions are preferably in the form of suppositories, tablets, capsules, powders, granules, microgranules, containing, in addition to the active ingredient and the effervescent agent, such carriers as are known in the art. For vaginal, administration, the compositions are preferably in the form of suppositories, vaginal rings, tablets, capsules, powders, granules, microgranules, containing, in addition to the active ingredient and the effervescent agent, such carriers as are known in the art. The suppositories and vaginal rings may be of a type that dissolve completely in the rectum or vagina, respectively, or remain intact following release of the composition, and subsequently removed. In general, the compositions may be prepared by mixing the ingredients using techniques well known to those skilled in the art for producing these dosage forms and for preparing effervescent pharmaceutical compositions, in which the effervescent materials must remain unreacted prior to administration of the composition.

In a preferred embodiment, the composition is administered in the form of a tablet. The tablets may, optionally, have special shapes to assist insertion of the compressed dosage form. These shapes include oval, capsule-shaped, and diamond-shaped tablets. An applicator device may also be supplied with the tablets to make insertion easier and to facilitate insertion deep into the rectal or vaginal cavity. Such applicators are commonly used in the pharmaceutical industry for this purpose.

The tablets may be matrix tablets, layered tables in which the various components are separated in different layers, or other specialized forms of tablets. The tablets are preferably manufactured by direct compression or any other tablet manufacturing technique known in the art. See, e.g., U.S. Pat. Nos. 5,178,878 and 5,223,264, which are incorporated by reference herein. Excipient fillers can be used to facilitate tableting. A filler desirably will also assist in the rapid dissolution of the dosage form. Nonlimiting examples of suitable fillers include mannitol, dextrose, lactose, and sucrose. Pellets or other multiparticulates may be manufactured by granulation, layering techniques, extrusion and spheronization or other pellet manufacturing methods. Granules may be made by dry granulation process or any other granulation process known in the art. Capsules can be soft gelatin capsules, hard gelatin capsules and the like made according to methods well known in the art.

In another preferred embodiment, the composition is administered in the form of a suppository. These are solid, molded units that are formed by pouring into suitable molds a molten wax or fatty material or other suitable substance as the base, into which is dissolved or dispersed the active ingredient and the effervescent penetration agent, and optionally, the pH adjusting substance, noneffervescent penetration enhancers and other excipients. Upon cooling, the base forms a solid containing the active ingredient and other ingredients dispersed in it and takes the shape of the mold. Examples of bases that could be used are cocoa butter, polyethylene glycols, polyvinyl pyrrolidone, gelatin, gelatin/glycerin combinations, esterfied fatty acids, polyoxyethelene sorbitans and polyoxyethylene sorbitan fatty acid esters. Various additives may be incorporated including surfactants and absorption enhancers such as medium chain (C8 to C12) fatty acids and fatty acid esters including mono-, di-, and triesters of glycol. Various bases, which may contain mixtures of different components, are also available. Examples of these are those sold under the trade names Imhausen, Witepsol and Gelucire. Various grades of each of these are available for specific applications. Mixtures of various bases may also be utilized in order to obtain a suppository with the required properties. Other shaping methods for forming the suppositories including cold molding and compression may also be used.

In a more preferred embodiment, a suppository of the present invention may be comprised of a suitable polyethylene glycol suppository base known in the art. More preferably, the polyethylene glycol suppository base is comprised of polyethylene glycol and polysorbate. A suitable commercially available polyethylene glycol suppository base is POLYBASE, manufactured by Paddock Laboratories, Inc. The polyethylene glycol suppository base is present in the suppository-based delivery system in any suitable amount so as to allow the composition to be in contact with the rectal or vaginal mucous membrane, respectively. The polyethylene glycol suppository base confers a degree of miscibleness with the mucous membrane surfaces of the rectum or vagina, wherein suspended particles of the compositions are in contact with such mucous membrane surfaces.

The suppository is preferably inserted into a laminate suppository shell which forms a molded shape. The suppository is stored in the shell until used. The laminate suppository shell is any shell known in the art suitable for packaging of the suppository. The suppository shell must be able to withstand temperatures of 60° C. used in manufacturing the suppositories and temperatures of 4° C. for long-term storage without compromising the integrity of the mold or reacting with the suppository in an unfavorable manner. Preferably, the laminate suppository shell is a polyvinyl chloride-polyethylene laminate suppository shell. A suitable commercially available laminate suppository shell is a polyvinyl chloride-polyethylene laminate suppository shell manufactured by Paddock Laboratories, Inc.

The compositions may be formulated for rapid, immediate, delayed or sustained release or a combination of these release forms. For delayed or sustained release, for example, the active ingredient and the effervescent agent may be combined with one or more coatings, matrix materials or membranes, which prevent exposure of the active ingredient and the effervescent agent to the environment of the rectum or vagina, until a predetermined time or predetermined event. Suitable coating and matrix materials, include, for example, materials which are responsive to pH changes, materials which are metabolized by enzymes present in the rectum or vagina, respectively, and materials which dissolve after a predetermined time or exposure to a certain volume of liquid.

The active ingredients suitable for use in the present invention include any active agent suitable for delivery by either the rectum or the vagina, as desired. Pharmaceutical ingredients suitable for use in the present dosage forms may include, without limitation, analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers; peptides, proteins, oligonucleotides and other substances of biological origin, and combinations thereof. Also encompassed by the term "active ingredient" are vitamins, minerals and dietary supplements as the same are defined, for example, in U.S. Pat. No. 5,178,878, the disclosure of which is also incorporated by reference herein.

More preferably, the active ingredients are drugs that display poor bioavailability, slow absorption or long $t_{max}$. These active ingredients include small molecule drugs, nutritional supplements (such as vitamins and minerals), proteins and peptides and other substances of biological origin. Examples of such drugs include, but are not limited to, the following:

| Drug | Bioavailability (%) |
|---|---|
| Acyclovir | 15–30 |
| Auranofin | 15–25 |
| Bretylium | 23 ± 9 |
| Cyclosporine | 23 ± 7 |
| Cytarabine | 20 |
| Doxepin | 27 ± 10 |
| Doxorubicin | 5 |
| Hydralazine | 16–35 |
| Ketamine | 20 ± 7 |
| Labetalol | 18 ± 5 |
| Mercaptopurine | 12 ± 7 |
| Methyldopa | 25 ± 16 |
| Nalbuphine | 25 ± 16 |
| Naloxone | 2 |
| Pentoxifylline | 19 ± 13 |
| Pyridostigmine | 14 ± 3 |
| Terbutaline | 14 ± 2 |
| Verapamil | 22 ± 8 |
| Riboflavin | 11 |
| Atenolol | 50 |

Other ingredients or techniques may preferably be used with the present compositions to enhance the dissolution and absorption of the pharmaceutical ingredient and/or to improve the disintegration profile. These include, but are not limited to, the use of additional chemical penetration enhancers and materials that aid in release and/or penetration of the drug in the rectum or vagina, respectively. There are various mechanisms by which such materials promote release and penetration of the active ingredient, and this invention is not limited to any one mechanism.

A bioadhesive polymer may preferably be included in the drug delivery device to increase the contact time between the dosage form and the rectal or vaginal mucosa. Nonlimiting examples of known bioadhesives used in the present invention include: carbopol (various grades), sodium carboxy methylcellulose, methylcellulose, polycarbophil (Noveon AA-1), hydroxypropyl methylcellulose, hydroxypropyl cellulose, sodium alginate, and sodium hyaluronate.

Disintegration agents may also be employed to aid in dispersion of the drug in the rectum or vagina, respectively. Disintegration agents include, for example, any pharmaceutically acceptable effervescent agent. In addition to the effervescence-producing disintegration agents, a dosage form according to the present invention may include suitable noneffervescent disintegration agents. Nonlimiting examples of disintegration agents include, for example, microcrystalline cellulose, croscarmelose sodium, crospovidone, starches and modified starches.

Other excipients may be employed, such as fillers, agents used to insure homogeneity of the composition and agents used to aid in preparation, as are well-known in the art.

Various modifications of the invention described herein will become apparent to those skilled in the art. Such modifications are intended to fall within the scope of the appending claims.

We claim:

1. A method for delivering an active ingredient to a target area in the rectum of a mammal; comprising the steps of:
    (a) administering in the rectum of a mammal a dosage form comprising a therapeutically effective amount of an active ingredient and at least one effervescent penetration enhancer present in an amount sufficient to increase absorption of said active ingredient across a mucosa layer of said target area,
    (b) causing said active ingredient and said effervescent penetration enhancer to release from said dosage form at said target area in said rectum and to provide effervescent action at said target area; so that said effervescent action promotes the absorption of a therapeutically effective amount of said active ingredient across said target area.

2. The method of claim 1 wherein said amount of said at least one effervescent penetration enhancer is about two times to about three times the amount of said active ingredient.

3. The method of claim 1, further comprising the step of administering a suitable pH adjusting substance in said dosage form.

4. The method of claim 1, further comprising the step of administering a bioadhesive in said dosage form, wherein said bioadhesive increases contact time between said active ingredient and a mucosa layer of said target area.

5. The method of claim 4, wherein said bioadhesive is contained in a portion of said dosage form external to said active ingredient.

6. The method of claim 1, further comprising the step of administering at least one noneffervescent disintegration agent in said dosage form.

7. The method of claim 1, wherein said dosage form is a suppository.

8. The method of claim 1, wherein said effervescent penetration enhancer comprises a pharmaceutically acceptable effervescent couple; said effervescent couple comprising an acid or equivalent thereof and a base or equivalent thereof.

9. The method of claim 8, wherein said base or equivalent thereof is present in an amount equal to about two times to about three times the amount of said active ingredient; and said acid is present in an amount approximately equimolar to said base.

* * * * *